United States Patent [19]

Davis

[11] Patent Number: 5,766,578
[45] Date of Patent: Jun. 16, 1998

[54] AXILLARY MALODOR NEUTRALIZATION

[75] Inventor: Iris J. Davis, Gaithersburg, Md.

[73] Assignee: The Gillette Company, Boston, Mass.

[21] Appl. No.: 475,820

[22] Filed: Jun. 7, 1995

Related U.S. Application Data

[62] Division of Ser. No. 240,208, May 9, 1994, which is a continuation of Ser. No. 911,872, Sep. 26, 1986, abandoned.

[51] Int. Cl.$^6$ ....................................................... A61K 7/32
[52] U.S. Cl. ........................... 424/65; 514/23; 514/381; 514/418; 514/475; 514/547; 514/557
[58] Field of Search ..................... 424/65; 514/23, 514/381, 418, 475, 547, 557

[56] References Cited

U.S. PATENT DOCUMENTS

| | | |
|---|---|---|
| 3,928,557 | 12/1975 | Wright ............................ 424/65 |
| 4,090,013 | 5/1978 | Ganslaw et al. .................. 424/65 |
| 4,110,430 | 8/1978 | Hopp et al. ...................... 424/65 |
| 4,263,274 | 4/1981 | Kulkarni et al. .................. 424/65 |
| 4,264,586 | 4/1981 | Callingham et al. ............. 424/65 |
| 4,294,821 | 10/1981 | Neumiller ......................... 424/65 |
| 4,382,919 | 5/1983 | Alonso et al. .................... 424/65 |

OTHER PUBLICATIONS

Leslie et al, 1962, vol.57, pp.3731i & 3732a, Chemical Abstracts.
Lee et al, 1963, vol.58, p. 9547e, Chemical Abstracts.
Lee et al(I), 1964, vol.60, p.385f, Chemical Abstracts.
Ellis, 1969, vol.70, p. 64960r, Chemical Abstracts.

*Primary Examiner*—Shelley A. Dodson
*Attorney, Agent, or Firm*—Burns, Doane, Swecker & Mathis, LLP

[57] ABSTRACT

A method of neutralizing axillary malodor by contacting the malodor with a sulfhydryl reactant.

10 Claims, No Drawings

AXILLARY MALODOR NEUTRALIZATION

This applications is a divisional of application Ser. No. 08/240,208, filed May 9, 1994, which is a continuation of application Ser. No. 06/911,872, filed Sep. 26, 1986, now abandoned.

BACKGROUND OF THE INVENTION

The present invention relates to compounds which neutralize axillary malodor.

Various approaches have been taken to the problem of axillary malodor. One approach has been the use of deodorants which may contain germicides and/or a fragrance. Germicides inhibit the reproduction of the bacteria which are believed to contribute to the production of axillary malodor. Fragrances are used to mask any odor produced. Another approach to the prevention of malodor is the use of antiperspirants. Antiperspirants inhibit bacteria and reduce the amount of sweat production thereby limiting the formation of substrate which gives rise to axillary malodor.

Certain metals and metal salts have been suggested for use in the control of odors. For example, Japanese Disclosure No. 83-222011 describes a cream for removing odor from the axilla which includes copper powder and perfume in a base of cosmetic cream. The disclosure postulates that the copper powder acts on the secretion of the odor, thereby suppressing generation of the malodor.

Another description of the use of metal salts against odors appears in French Patent No. 1,394,875. This French patent describes the use of water-soluble iron and copper compounds to reduce or eliminate body odors. Various salts and complexes of cupric copper and ferrous iron are mentioned, including sulfates, chlorides, acetates, gluconates, citrates, tartrates, salts of ethylenediamine tetraacetic acid sodium or potassium, and iron and copper chlorophyllins. Various iron and copper phosphates are also mentioned, especially for use as food additives. The most effective combinations are indicated to be those in which both metals are present in the ionizable and nonionizable forms. The only testing reported in the French patent was odor reduction of sewage sludge, and odor reduction in mice by measurement of the odor of the entire mouse, fecal odor and urine odor.

German Patent No. 1,083,503 describes the deodorizing action of metal complexes of 1,3-diketones. Listed metals include copper, nickel, cobalt, calcium, zirconium, zinc, tin, aluminum, cadmium, cerium, beryllium, magnesium, and mercury. Their use in various ways, including topical application to the axilla, is discussed. These compounds are theorized to function by interfering with the metabolism of the odor-producing microorganisms.

British Patent Application No. 1,581,586 describes a sanitary foot wear article which includes a composition comprising copper, silver, or a copper-silver alloy powder dispersed in and held by water-insoluble resin binder. The British patent application indicates a belief that the metal reacts with substances secreted by the foot to produce metal salts which act as astringents and also act to prevent the growth of microorganisms.

Despite the above, attempts have continued to find compositions which are effective against axillary malodor even after it has been formed.

SUMMARY OF THE INVENTION

The present invention is a method of neutralizing axillary malodor by contacting the malodor with a sulfhydryl reactant.

DETAILED DESCRIPTION OF THE INVENTION

The present invention includes the surprising discovery that certain compounds effectively neutralize preformed axillary malodor. This should be contrasted with the prior art where the focus was on either preventing formation of the odor, or on masking it after production. This distinction is particularly important in treating axillary malodor build-up in certain fabrics, particularly polyesters.

As a part of the attempt to identify the malodor compound, numerous compounds have been tested to determine their ability as malodor neutralizers. This has led to the unexpected and surprising discovery that relatively few compounds are effective in neutralizing axillary malodor. Moreover, many compounds which have previously been suggested as deodorants do not act as neutralizers. The compounds which are effective as neutralizers are sulfhydryl reactants. By sulfhydryl reactant is meant a compound which chemically reacts with a sulfhydryl group to form a covalent bond. Compounds effective in malodor neutralization are listed in Table I. The compounds indicated have been confirmed subjectively, i.e., by a sniff test described further below.

Table I

In aqueous solution.
N-ethylmaleimide
Diethyl fumarate in base
Di-n-butyl maleate in base
Iodoacetic acid
Alginic acid
2,3,5-triphenyl-2H-tetrazolium chloride
In alcohol
N-coumarylmaleimide
Dansyl aziridine Although Table I lists only specific maleimides and a specific aziridine, maleimides and aziridines in general are sulfhydryl reactants and would be expected to be effective odor neutralizers.

The indication in Table I that diethyl fumarate and di-n-butyl maleate are "in base" should also be noted. These two compounds are not effective neutralizers in acidic or neutral media. Although only a single fumerate and maleate are listed in Table I, dialkyl fumarates and maleates wherein each alkyl is one to about eight carbon atoms would be expected to be effective odor neutralizers.

One confirmation that reaction with a sulfhydryl group is involved is that relatively closely related compounds such as dibutyl succinate are not effective neutralizers because they do not react to form covalent bonds with sulfhydryl groups.

The compounds of the present invention can be applied to the axilla in any of the various cosmetically-acceptable delivery systems well known to those skilled in the art. These include deodorant sticks, microencapsulation in a suitable base, dual dispensers, powders, and aerosols in non-aqueous suspensions. Any of the commonly employed ingredients can be used, provided they have no adverse effect on the active ingredient(s).

The concentration of the malodor neutralization compound can vary over a wide range depending on which compound is being employed. Typical concentrations are between about 0.001 and about 100% by weight, preferably between about 0.05 and about 5.0%. In the case of aqueous N-ethylmaleimide and alcoholic N-coumarylmaleimide, the preferred concentration is about 2% wt/vol. When alcohol is used as the vehicle, the preferred alcohols are ethanol and isopropanol.

The neutralizers of the present invention would also be effective to neutralize axillary malodor in fabrics. As discussed above, one of the problems with prior art methods of dealing with axilla malodor was that no method was available for removing the odor from synthetic fabrics. 100% polyester clothing is particularly prone to irreversible absorption of axillary malodor. Such absorption is also seen in cotton/polyester blends. By "irreversible" is meant that the odor is retained even after repeated laundering with detergent. Moreover, soil-release-finished polyester fabric retains malodor even more stubbornly than unfinished polyester.

In particular, N-ethylmaleimide and N-coumarylmaleimide would be expected to be effective in malodor neutralization when employed at 2.0% by weight based upon the weight of the laundering bath.

The compound employed for malodor neutralization in fabrics can either be added separately, as a powder or liquid formulation, or incorporated as an additional ingredient in known laundry detergents. Care should be exercised to ensure that no adverse interaction occurs between the detergent and the malodor neutralization compound, particularly when the detergent includes phosphates.

In order to further illustrate the present invention and the advantages thereof, the following specific examples are given, it being understood that these examples are intended only to be illustrative without serving as a limitation on the scope of the present invention.

EXAMPLES

The following description sets forth the preparation of malodor samples, and the procedure for identifying malodor neutralizers.

Preparation of Malodor Samples

Aqueous axillary samples were collected daily from a panel of known malodor substrate producers. These odorless samples were pooled, extracted with hexane to remove lipid material and lyophilized. The dry samples were then inoculated with axillary odor-producing bacteria in 10mL distilled water to yield aqueous solutions of acrid malodor. Aliquots of 1–3 ml aqueous malodor were used for malodor neutralization experiments. The larger sample size was used if the level of malodor observed in the headspace of the sample was low.

Procedure for Identifying Malodor Neutralizers

Three drops of reagent in water or ethanol were added to 1–3 mL aliquots of aqueous malodor in a 4mL vial. Approximately 0.5-1 mL of chloroform was added to the vial. The sample was inverted several times. The two layers were allowed to separate for a few minutes. Aliquots of the chloroform layer were removed and evaluated for odor. Controls were prepared in the same manner except that three drops of deionized water were used in place of reagent. This extraction technique resulted in concentration of the malodor in the chloroform layer.

Measurement of Odor

Approximately 10 microliters of the chloroform layer were blotted on filter paper. The paper was sniffed for odor after evaporation of the solvent.

Product types suitable for application to the axilla to neutralize malodor include aqueous alcoholic solutions, lotions, creams, ointments, powders, suspensions, soaps, waxes, gels, stick forms and compositions for pressurized dispensing in the form of an aerosol. The following examples are exemplary of such product types.

Example 1

| Aerosol: | Wt. % |
| --- | --- |
| N-ethylmaleimide | 1.0 |
| Isopropyl myristate | 3.7 |
| Fumed Silica | 0.15 |
| Perfume | 0.25 |
| Propellants | 94.9 |

Example 2

| Roll-On: | |
| --- | --- |
| Cetyl alcohol | 2.0 |
| Acetylated lanolin (A-lan) | 2.0 |
| 30% Lanolin alcohol/mineral oil solution | 5.0 |
| Peg 40 stearate | 4.0 |
| Glycerin | 2.0 |
| Propylparaben | 0.02 |
| Magnesium aluminum silicate (Veegum HV) | 1.0 |
| Water | 83.3 |
| Methylparaben | 0.18 |
| N-ethylmaleimide | 0.5 |
| Perfume | q.s. |

Example 3

| Creme: | Wt. % |
| --- | --- |
| Mineral Oil | 2.2 |
| Hexadecyl isostearate | 1.0 |
| Di-octyldodeceth-2-lauroyl glutamate (Amiter LGOD-2) | 1.0 |
| Hydrogenated lanolin | 0.2 |
| Oleth-4 | 0.6 |
| Oleth-10 | 0.6 |
| PEG-40 hydrogenated castor oil PCA isostearate (Pyroter CPI-40) | 0.3 |
| Glyceleth-25 PCA isostearate (Pyrother CPI-25) | 0.5 |
| Propylene glycol | |
| N-ethylmaleimide | 0.5 |
| Ethyl alcohol | 5.0 |
| Methylparaben | q.s. |
| Water | 86.4 |

Example 4

| Stick: | |
| --- | --- |
| Sodium stearate | 7.0 |
| Glyceryl isostearate (Imwitor 780) | 3.0 |
| PEG-6 caprylic/capric glycerides (Softigen 767) | 12.0 |
| 1,2-propylene glycol | 8.0 |
| Glycerin | 5.0 |
| Water | 20.0 |
| N-ethylmaleimide | 0.5 |
| Ethanol, 96% | 43.5 |
| Perfume Oil Deosafe 75 428N/II | 1.0 |

Although the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A composition for neutralizing axillary malodor comprising at least one neutralizing compound which is a sulfhydryl reactant in a cosmetically acceptable vehicle.

2. The composition of claim 1 wherein the sulfhydryl reactant is a maleimide, an aziridine, dialkyl fumarate in base, dialkyl maleate in base, iodoacetic acid, alginic, or 2,3,5-triphenyl-2H-tetrazolium chloride.

3. The composition of claim 1, wherein the sulfflydryl reactant is a maleimide.

4. The composition of claim 3, wherein the maleimide is N-ethylmaleimide or N-coumarylmaleimide.

5. The composition of claim 4, wherein the neutralizing compound is N-ethylmaleimide or N-coumarylmaleimide present at a concentration of about 2% wt/vol.

6. The composition of claim 1 wherein the sulfhydryl reactant is an aziridine.

7. The composition of claim 6 wherein the aziridine is dankly aziridine.

8. The composition of claim 1 wherein the sulfhydryl reactant is diethyl fumarate in base or di-n-butyl maleate in base.

9. The composition of claim 1 wherein the neutralizing compound is present at a concentration of at least about 0.001% by weight.

10. The composition of claim 1 wherein the neutralizing compound is present at a concentration between about 0.05 and about 5.0% by weight.

* * * * *